United States Patent [19]

Fumaux et al.

[11] 4,246,074

[45] Jan. 20, 1981

[54] PROCESS FOR THE SEPARATION OF A MIXTURE OF CHLOROACETYL CHLORIDE AND DICHLOROACETYL CHLORIDE

[75] Inventors: Eric Fumeaux; Christoph Zinsstag; Roland Delseth, all of Visp,, Switzerland

[73] Assignee: Lonza Ltd., Gampel, Valais, Switzerland

[21] Appl. No.: 2,385

[22] Filed: Jan. 10, 1979

Related U.S. Application Data

[63] Continuation-in-part of Ser. No. 868,739, Jan. 12, 1978, abandoned.

[30] Foreign Application Priority Data

Jan. 13, 1977 [CH] Switzerland .......................... 391/77

[51] Int. Cl.³ .......................... C07C 53/48; B01D 3/40
[52] U.S. Cl. ...................................... 203/70; 203/78; 203/91; 260/544 Y
[58] Field of Search ............... 260/544 Y; 203/70, 78, 203/91

[56] References Cited

U.S. PATENT DOCUMENTS

| | | | |
|---|---|---|---|
| 3,763,023 | 10/1973 | Horsley | 203/63 |
| 3,950,415 | 4/1976 | Bressel | 260/544 Y |

OTHER PUBLICATIONS

*Unit Operations,* Brown, (1951), pp. 393–394.
Azeotropic and Extractive Distillation, Chem. Eng. Progress, vol. 65, No. 9, Gerster, 9/69, pp. 43–46.
"Chemical Engineers Handbook", 5th Ed., pp. 13-43.

*Primary Examiner*—Wilbur L. Bascomb, Jr.
*Attorney, Agent, or Firm*—Fisher, Christen & Sabol

[57] ABSTRACT

Process for the separation of a mixture of chloroacetyl chloride and dichloroacetyl chloride by extractive distillation. The mixture of chloroacetyl chloride and dichloroacetyl chloride is treated with n-dodecane, which is a saturated aliphatic hydrocarbon extraction agent. Lower levels of dichloroacetyl chloride contaminant are achieved than by prior art processes.

11 Claims, 2 Drawing Figures

PROCESS FOR THE SEPARATION OF A MIXTURE OF CHLOROACETYL CHLORIDE AND DICHLOROACETYL CHLORIDE

This is a continuation-in-part of U.S. Application Ser. No. 868,739, filed on Jan. 12, 1978 and now abandoned.

BACKGROUND OF THE INVENTION

1. Field of This Invention

This invention relates to a process for the separation by extractive distillation of a mixture of chloroacetyl chloride and dichloroacetyl chloride.

2. Prior Art

From U.S. Pat. No. 3,763,023 it has been known to separate chloroacetyl chloride from dichloroacetyl chloride by azeotropic distillation with the help of a hydrocarbon boiling at 90° to 130° C. With diallyl ether, a minimum dichloroacetyl chloride content of 2.1 percent is achieved in the distillate. U.S. Pat. No. 3,763,023 states:

"Operable azeotrope-forming compounds have a boiling point at atmospheric pressure of about 90° to 130° C., preferably about 95° to 120° C., and are hydrocarbons, halogenated by hydrocarbons and aliphatic ethers. A mixture of related compounds such as a saturated aliphatic hydrocarbon fraction having a boiling range within the defined limits can also be used." [Emphasis supplied] [Col. 1, lines 40 to 47]

The use of the term "operable" by such U.S. patent in defining the azeotrope former teaches one ordinarily skilled in the art not to even try similar compounds which have a boiling point outside of the range of 90° to 130° C.

Another process for the production of chloroacetyl chloride is described in German Pat. No. 2,313,405. U.S. Pat. No. 3,950,415 is an English language equivalent of German Pat. No. 2,313,405. A mixture of chloroacetyl chloride and dichloroacetyl chloride is distilled in the presence of water or alkanols with up to 4 carbon atoms. According to Example 1, a content of 2.11 percent by weight of dichloroacetyl chloride is reduced to 1.4 percent by weight; the yield of chloroacetyl chloride amounts to 83 percent by weight. According to Example 2, the dichloroacetyl chloride content is reduced from 1.2 to 0.78 percent by weight, with a yield of chloroacetyl chloride of 85 percent by weight.

In many types of useage of chloroacetyl chloride, a dichloroacetyl chloride content of more than 0.5 percent by weight is disturbing. The known separation processes, for example, that of U.S. Pat. No. 3,763,023, are not capable of producing such pure products and a step-by-step achievement of the required values, for example, according to German Pat. No. 2,313,405, would be achievable (if it were possible at all) only with great loss of chloroacetyl chloride.

See also: Brown, George G., "Unit Operations", John Wiley & Sons, Inc., (1951), pp. 393-394; Gerster, J. A., "Azeotropic and Extractive Distillation", Chemical Engineering Progress, Vol. 65, No. 9 (September 1969), pp. 43-46; Perry (Ed.), "Chemical Engineer's Handbook", 5th Ed., McGraw Hill, pp. 13-43; and Krell, Erich, "Handbuch der Laboratoriumsdistillation", Vol. 1, No. 2, p. 306.

BROAD DESCRIPTION OF THE INVENTION

An object of this invention is to provide a process for separating dichloroacetyl chloride from chloroacetyl chloride whereby the level of residual dichloroacetyl is less than that achieved by prior art separation processes. Other objects and advantages of this invention are set out herein or are obvious herefrom to one ordinarily skilled in the art.

The objects and advantages of this invention are achieved by the process of this invention.

This invention involves the fact that chloroacetyl chloride can be obtained with a content of dichloroacetyl chloride of below 0.5 percent by weight by means of extractive distillation. This invention achieves such through the process where a mixture of chloroacetyl chloride and dichloroacetyl chloride is treated (extractively distilled) with n-dodecane, which is a saturated aliphatic hydrocarbon extraction agent.

The n-dodecane extraction agent can be added in doses, effectively at the upper end of the distillation column; and the mixture of chloroacetyl chloride and dichloroacetyl chloride can be added in doses in the lower half of the column. Effectively, a distillation column with 10 to 60 theoretical plates is used. The dosing in of the n-dodecane extraction agent at the upper end of the distillation column means that the extraction agent is added in the area of the uppermost or the second uppermost theoretical plate of the distillation column. The dosing in of the mixture of chloroacetyl chloride and dichloroacetyl chloride into the lower half of the column means that the mixture is fed into a place in the distillation column which, expressed in numbers and counted from below, corresponds at most to half of the theoretical number of plates.

The quantity of n-dodecane extraction agent per se is not critical. The more n-dodecane extraction agent that is used, the better the separation. However, the capacity of the installation will drop with an increasing quantity of extraction agent. On the other hand, with too small of a quantity of extraction agent, the content of dichloroacetyl chloride in the distillate increases. Effectively, the ratio of n-dodecane extraction agent to distillate is from 5:1 to 30:1.

The process according to this invention can be carried out at standard or lower pressure. Because the low boiling points of chloroacetyl chloride and dichloroacetyl chloride are very low at a very low pressure and because of the chemical decomposition at temperatures which occur at increased pressure, the process of this invention is effectively carried out between 20 torr and standard pressure, preferably between 50 and 100 torr.

According to the process of this invention, it is possible to distill chloroacetyl chloride with a content of at most 0.1 percent dichloroacetyl chloride at the head of the column. Dichloroacetyl chloride remains behind in the nodule with the n-dodecane extraction agent. The n-dodecane extraction agent can be freed continuously by standard chloride distillation in vacuum of dichloroacetyl chloride and of the residual chloroacetyl chloride, and can be returned without evaporation of the extraction column.

According to the process of this invention, chloroacetyl chloride is achieved as an end product with a content of dichloroacetyl chloride contaminant of below 0.5 percent by weight from a raw product having a content of up to 10 percent by weight of dichloroacetyl chloride.

DETAILED DESCRIPTION OF THIS INVENTION

Figure 1:
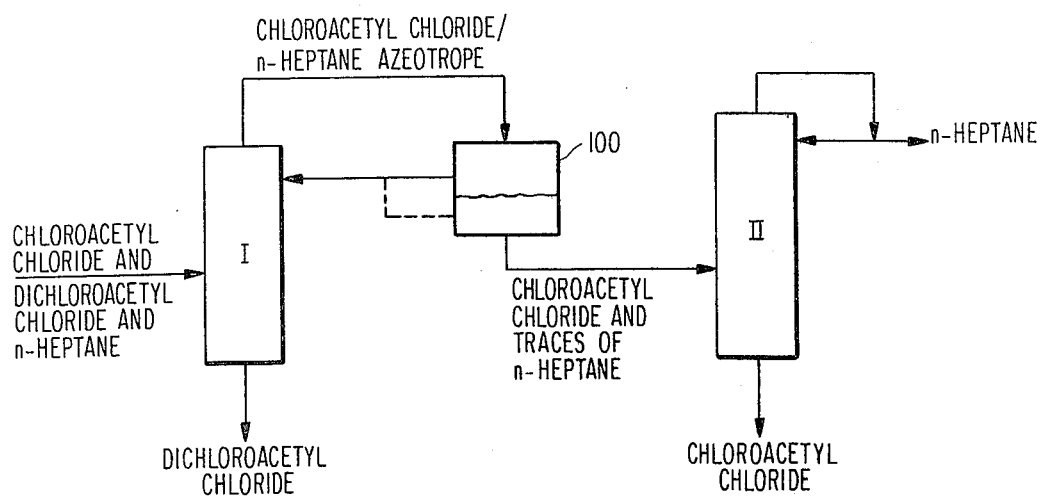

As used herein, all parts, ratios and percentages are on a weight basis unless otherwise stated herein or otherwise obvious herefrom to one ordinarily skilled in the art.

Figure 2:
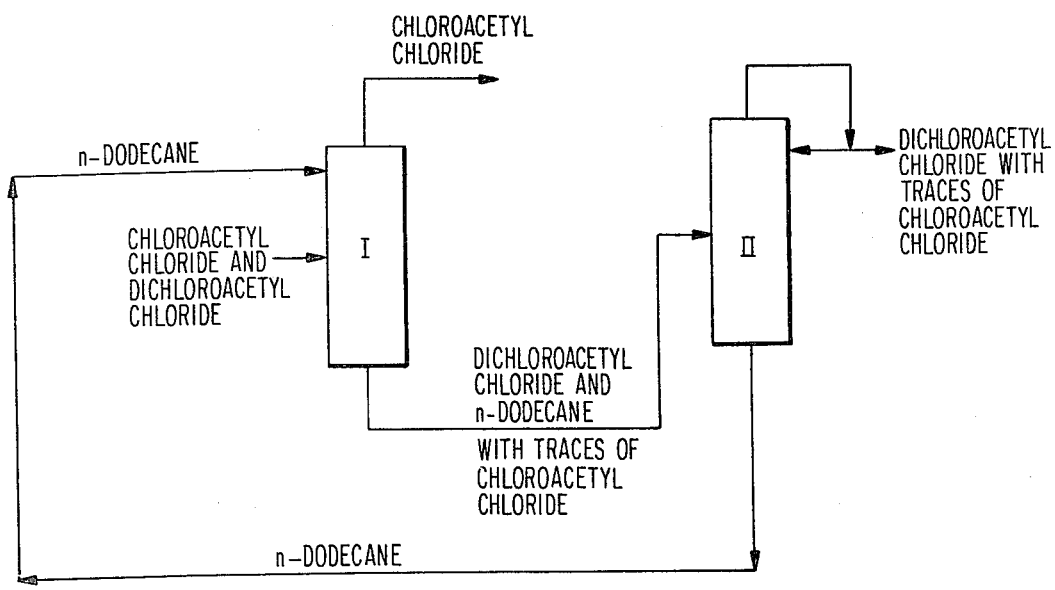

In the drawings:

FIG. 1 is a schematic diagram of the azeotropic distillation of n-heptane in Example 5; and FIG. 2 is a schematic diagram of the extractive distillation of n-dodecane in Example 5.

EXAMPLE 1

A mixture of 95 percent of chloroacetyl chloride and 5 percent of dichloroacetyl chloride was continuously extractively distilled in a column of about 20 theoretical plates using n-dodecane. The extraction agent was added to the column at a theoretical plate and the mixture of chloroacetyl chloride and dichloroacetyl chloride at 11 theoretical plates below the head of the column. The reflux ratio was 1:1 and the pressure at the head of the column was 50 torr. The ratio of the quantity of extraction agent to the quantity of distillate was 12 to 1. The content of dichloroacetyl chloride in the chloroacetyl choride in the distillate was 0.45 percent by weight. The loss of chloroacetyl chloride in the nodule was 6 percent.

EXAMPLE 2

A mixture of 95 percent of chloroacetyl chloride and 5 percent of dichloroacetyl chloride was continuously and extractively distilled with n-dodecane as in Example 1. The pressure at the head of the column was 50 torr and the ratio of the quantity of extraction agent to the quantity of distillate was 20:1. The content of dichloroacetyl chloride in the distillate was 0.1 percent by weight and the ratio of chloroacetyl chloride to dichloroacetyl chloride in the nodule was 1:1.

EXAMPLE 3

A mixture of 90 percent of chloroacetyl chloride and 10 percent of dichloroacetyl chloride was continuously and extractively distilled using n-dodecane in a column of 30 theoretical plates and otherwise as in Examples 1 and 2. The pressure at the head of the column was 50 torr and the ratio of the quantity of extraction agent to the quantity of distillate was 20 to 1. The content of chloroacetyl chloride in the distillate was less than 0.5 percent by weight.

EXAMPLE 4

A mixture of 95 percent of chloroacetyl chloride and 5 percent of dichloroacetyl chloride was continuously and extractively distilled using n-dodecane in the same column used in Examples 1 and 2. The ratio of the quantity of extraction agent to the quantity of distillate was 8 to 1. The content of dichloroacetyl chloride at the head of the column was 0.5 percent by weight and the ratio of chloroacetyl chloride to dichloroacetyl chloride in the nodule was 1 to 1. In the case of the pressure used in this example, the n-dodecane was discolored so that it had to be distilled prior to further use.

EXAMPLE 5

Azeotropic distillation was affected in the system of FIG. 1. The additive material, n-heptane, was mixed with a mixture of 90 weight percent of chloroacetyl chloride and 10 weight percent of dichloroacetyl chloride. The mixture of the three components was fed into the first column (I). The n-heptane additive and chloroacetyl chloride were evaporated in column I and passed into phase separator 100. Almost all of the n-heptane additive was sent back into column I. 59 percent [i.e., (10−4.1)/100] of the dichloroacetyl chloride contaminant was removed from the bottom of column I. The chloroacetyl chloride and a trace of n-heptane was sent into column II, where the chloroacetyl chloride came off the bottom and the n-heptane came off the top. A considerable amount of dichloroacetyl chloride contaminant was left in the recovered chloroacetyl chloride.

Extractive distillation was affected in the system of FIG. 2, which did not require a phase separator as did the azeotropic distillation system of FIG. 1. The extraction agent, n-dodecane, and a mixture of 95 weight percent of chloroacetyl chloride and 5 weight percent of dichloroacetyl chloride were fed into the first column I. The chloroacetyl chloride came off the top of column I. The n-dodecane extraction agent was not evaporated, but was washed out the bottom of column I with the dichloroacetyl chloride. 90 percent [i.e., (5−0.5)/100] of the dichloroacetyl chloride was removed from the chloroacetyl chloride using extractive distillation-a far lower percentage of contaminent was removed using azeotropic distillation. The n-dodecane and dichloroacetyl chloride containing traces of chloroacetyl chloride were sent to column II, where the dichloroacetyl chloride came came off the top and the n-dodecane came off the bottom (and was recycled to column I).

Certain thermodyanamic data for the various components used is:

| Component | B. P., °C. | ΔH$_\nu$Kcal/kg |
|---|---|---|
| chloroacetyl chloride | 107° | 76.2 |
| dichloroacetyl chloride | 108° | 58.4 |
| n-heptane | 98.4° | 80.0 |
| n-dodecane | 214.5° | 61.3 |

The following is an estimate of the power consumption for the purification of 100 kg. of chloroacetyl chloride using the azeotropic distillation system and the extractive distillation system. In the head of column I of the azeotropic distillation system, for 45 percent chloroacetyl chloride (i.e., for 100 kg of chloroacetyl chloride), 122 kg of n-heptane are required. For a reflux of 1:1, one requires 34,700 Kcal. (i.e., $Q = 200 \times 76.2 + 244 \times 80$). It is assumed the power consumption of column II is negligible. For the extractive distillation system, in column I there is no reflux, i.e., for 100 kg chloroacetyl chloride. In column II a reflux of 1:1 is used, i.e., on the 100 kg chloroacetyl chloride basis. $Q = 100 \times 76.2 \times 10 \times 58.4 = 8,204$ Kcal. The heat losses, in the case of the return of the n-dodecane, are ignored. The first heating of the n-dodecane is ignored. So it is estimated that the power consumption for the purification of 100 kg of chloroacetyl chloride using azeotropic distillation (n-heptane) is about 35,000 Kcal and using extractive distillation (n-dodecane) is about 10,000 Kcal.

What is claimed is:

1. Process for the separation of a mixture of chloroacetyl chloride and dichloroacetyl chloride by extractive distillation in a distillation column, characterized in that the mixture of chloroacetyl chloride and dichloroacetyl chloride is extractively distilled in the presence of n-dodecane, the extraction agent, the extraction agent being introduced into the upper end of the distillation column, the mixture of chloroacetyl chloride and dichloroacetyl chloride being introduced into the lower half of the distillation column, part of the chloroacetyl chloride, the distillate, being recovered out of the top of the distillation column, and the dichloroacetyl chloride, the n-dodecane and the residue chloroacetyl chloride being obtained at the bottom of the distillation column.

2. Process as claimed in claim 1 wherein the distillation column has 10 to 60 theoretical plates.

3. Process as claimed in claim 1 wherein the ratio of extraction agent to distillate is from 5:1 to 30:1.

4. Process as claimed in claim 1 wherein the extractive distillation is carried out between 20 torr and standard pressure.

5. Process as claimed in claim 1 wherein the extractive distillation is carried out between 50 to 100 torr.

6. Process as claimed in claim 1 wherein the recovered chloroacetyl chloride contains less than 0.5 percent by weight of dichloroacetyl chloride.

7. Process as claimed in claim 1 wherein the recovered chloroacetyl chloride contains at most 0.1 percent by weight of dichloroacetyl chloride.

8. Process as claimed in claim 1 wherein the distillation column has 10 to 60 theoretical plates, the ratio of the extraction agent to the distillate is from 5:1 to 30:1 and the extractive distillation is carried out between 20 torr and standard pressure.

9. Process as claimed in claim 1 wherein the extraction agent is removed by distillation under vacuum in a second distillation from the mixture of dichloroacetyl chloride, extraction agent and residual chloroacetyl chloride obtained from the bottom of the first distillation column.

10. Process as claimed in claim 9 wherein, without evaporation, the recovered extraction agent is cooled and recycled to the first distillation column, where the extractive distillation occurs.

11. Process as claimed in claim 10 wherein the distillation column, where the extractive distillation occurs, has 10 to 60 theoretical plates, wherein in the distillation column where the extractive distillation occurs, the ratio of the extraction agent to the distillate is from 5:1 to 30:1, and wherein the extractive distillation is carried out between 20 torr and standard pressure.

* * * * *